US006218366B1

(12) United States Patent
St. Cyr et al.

(10) Patent No.: US 6,218,366 B1
(45) Date of Patent: Apr. 17, 2001

(54) METHOD FOR RAISING THE HYPOXIC THRESHOLD

(75) Inventors: John St. Cyr, Coon Rapids; Clarence A. Johnson, Wyoming, both of MN (US); Dean J. MacCarter, Englewood, CO (US); Stephen G. Sawada, Indianapolis, IN (US)

(73) Assignee: Bioenergy, Inc., Ham Lake, MN (US)

( * ) Notice: Subject to any disclaimer, the term of this patent is extended or adjusted under 35 U.S.C. 154(b) by 0 days.

(21) Appl. No.: 09/406,266

(22) Filed: Sep. 24, 1999

Related U.S. Application Data

(63) Continuation-in-part of application No. 09/290,789, filed on Apr. 12, 1999.
(60) Provisional application No. 60/090,001, filed on Jun. 19, 1998.

(51) Int. Cl.$^7$ .................................................. A61K 31/70
(52) U.S. Cl. ............................................................ 514/23
(58) Field of Search ................................................ 514/23

(56) References Cited

U.S. PATENT DOCUMENTS

| | | | |
|---|---|---|---|
| 4,605,644 | 8/1986 | Foker | 514/45 |
| 4,719,201 | * 1/1988 | Foker | 514/23 |
| 4,824,660 | 4/1989 | Angello et al. | 424/1.1 |
| 4,871,718 | * 10/1989 | Carniglia | 514/23 |
| 4,920,098 | 4/1990 | Cotter et al. | 514/2 |
| 4,968,719 | 11/1990 | Brevetti | 514/556 |
| 5,114,723 | 5/1992 | Stray-Gundersen | 426/74 |
| 5,292,538 | 3/1994 | Paul et al. | 426/74 |
| 5,391,550 | 2/1995 | Carniglia et al. | 514/23 |
| 5,707,971 | 1/1998 | Fahy | 514/43 |
| 5,714,515 | 2/1998 | Bunger | 514/557 |

FOREIGN PATENT DOCUMENTS

| | | | |
|---|---|---|---|
| 4228215 | * 3/1994 | (DE) | 514/23 |
| 0312249 | 4/1989 | (EP) | A61K/33/08 |
| 0573466 | 12/1993 | (EP) | A61K/31/70 |
| 0680945 | 11/1995 | (EP) | C07C/229/22 |
| 94/02127 | 2/1994 | (WO) | A61K/31/195 |
| 96/18313 | 6/1996 | (WO) | A23L/1/305 |

OTHER PUBLICATIONS

Angello, D.A., et al., "Recovery of Myocardial Function and Thallium 201 Redistribution Using Ribose", *American Journal of Cardiac Imaging*, 3 (4), pp. 256–265, (Dec. 1989).
Batista, R., "Partial left ventriculectomy—the Batista procedure", *European Journal of Cardio–Thoracic Surgery*, 15 (Suppl. 1), pp. S12–S19, (Jan. 1999).
Bax, J.J., et al., "Accuracy of Currently Available Techniques for Prediction of Functional Recovery After Revascularization in Patients With Left Ventricular Dysfunction Due to Chronic Coronary Artery Disease: Comparison of Pooled Data", *Journal of the American College of Cardiology*, 30 (6), pp. 1451–1460, (Nov. 15, 1997).

Furnary, A.P., et al., "Multicenter Trial of Dynamic Cardiomyoplasty for Chronic Heart Failure", *Journal of the American College of Cardiology*, 28 (5), pp. 1175–1180, (Nov. 1, 1996).
Gross, M., et al., "Metabolism of D–Ribose Administered Continuously to Healthy Persons and to Patients with Myoadenylate Deaminase Deficiency", *Klin Wochenschr*, 67, pp. 1205–1213, (1989).
Gross, M., et al., "Ribose administration during exercise: effects on substrates and products of energy metabolism in healthy subjects and a patient with myoadenylate deaminase deficiency", *Klin. Wochenshr.*, 69, pp. 151–155, (1991).
Jessup, M., "Optimizing Medical Management of the Patient with Severe Heart Failure Awaiting Cardiac Transplantation", *Cardiology—In Review*, 4 (5), pp. 286–291, (Sep. 1996).
Mahoney, Jr., et al., "A comparison of different carbohydrates as substrates for the isolated working heart", *Journal of Surgical Research*, 47, pp. 530–534, (1989).
Pliml, W., et al., "Effects of ribose on exercise–induced ischaemia in stable coronary artery disease", *The Lancet*, 340, pp. 507–510, (Aug. 29, 1992).
Sawada, S.G., et al., "Echocardiographic Detection of Coronary Artery Disease During Dobutamine Infusion", *Circulation*, 83 (5), pp. 1605–1614, (May 1991).
Schultis, K., et al., "Xylitol in metabolism during stress conditions", *Medizin und Ernahrung*, 11 (3), Jahrgang, pp. 59–63, (1970).
St. Cyr, J.A., et al., "Enhanced high energy phosphate recovery with ribose infusion after global myocardial ischemia in a canine model", *Journal of Surgical Research*, 46 (2), pp. 157–162, (Feb. 1989).
Tan, Z.T., et al., "Verapamil ribose adenine enhance resynthesis of postischemic myocardial ATP", *Life Sciences*, 55 (18), pp. PL 345–PL 349, (1994).
Tullson, P.C., et al., "Adenine Nucleotide Syntheses in Exercising and Endurance–trained Skeletal Muscle", *The American Journal of Physiology*, 261 (2), pp. C342–C347, (1991).
Tullson, P.C., et al., "IMP Metabolism in Human Skeletal Muscle After Exhaustive Exercise", *The American Journal of Physiology*, pp. 146–152, (1995).

(List continued on next page.)

*Primary Examiner*—James H. Reamer
(74) *Attorney, Agent, or Firm*—Schwegman, Lundberg, Woessner & Kluth, P.A.

(57) ABSTRACT

The administration of ribose raises the hypoxic threshold of mammals experiencing a hypoxic condition. The presence of an effective amount of ribose in the tissue of a mammal increases the tolerance to hypoxia and decreases the symptoms of hypoxia in mammals experiencing chronic hypoxia due to cardiovascular disease or peripheral vascular disease. Such mammals are additionally benefited by administration of ribose and a vasodilator or an isotropic agent. Mammals experiencing transient hypoxia from high altitude, anesthesia or exercise are also benefited.

10 Claims, 3 Drawing Sheets

OTHER PUBLICATIONS

Wagner, D.R., et al., "Effects of oral ribose on muscle metabolism during bicycle ergometer in AMPD–deficient patients", *Annals of Nutrition and Metabolism*, 35 (5), pp. 297–302, (1991).

Zimmer, H.G., et al., "Ribose accelerates the repletion of the ATP pool during recovery from reversible ischemia of the rat myocardium", *Journal of Molecular and Cellular Cardiology*, 16 (9), pp. 863–866, (Sep. 1984).

Zollner, N., et al., "Myoadenylate Deaminase Deficiency: Successful Symptomatic Therapy by High Dose Oral Adminstration of Ribose", *Klin Wochenschr*, 64, pp. 1281–1290, (1986).

* cited by examiner

MEAN POWER PER SPRINT SESSION. CALCULATED AS AN AVERAGE OF THE MEAN POWER OF 15 SPRINTS DURING EACH SPRINT SESSION

FIG. 3

PEAK POWER PER SPRINT SESSION. CALCULATED AS AN AVERAGE OF THE PEAK POWER OF 15 SPRINTS DURING EACH SPRINT SESSION.

METHOD FOR RAISING THE HYPOXIC THRESHOLD

This application is a Continuation-in-part of application Ser. No. 09/290,789, filed on Apr. 12, 1999, which is a continuation of provisional application No. 60/090,001, filed Jun. 19, 1998 which issued as U.S. Pat. No. 6,159,942, on Dec. 12, 2000.

FIELD OF THE INVENTION

The present invention relates to compositions and methods for raising the hypoxic threshold in mammals experiencing a hypoxic condition. Such mammals include humans with cardiovascular or peripheral vascular disease, or humans undergoing chronic or transient hypoxia.

BACKGROUND OF THE INVENTION

It is well known that the energy coinage of the cell is adenosine triphosphate (ATP). During anabolism, the energy derived from the metabolism of nutrients is transferred to high energy phosphate bonds of ATP. The energy in these bonds is expended during the energy consumption phase. An important and "costly" expenditure, in which ATP is rapidly cycled, is that required for muscular contraction.

The energy buildup steps occur within the muscle cell during two basic processes. Oxidative phosphorylation replenishes ATP by the breakdown of circulating fatty acids, glucose and intramuscular glycogen and triglycerides. Anaerobic phosphorylation provides ATP from creatine phosphate, circulating glucose and intramuscular glycogen via kinase reactions such as the myokinase reaction.

In the synthesis of ATP via the nucleotide salvage pathway, the nucleotide precursors that may be present in the tissue are converted to AMP and further phosphorylated to ATP. Adenosine is directly phosphorylated to AMP, while xanthine and inosine are first ribosylated by 5-phosphoribosyl-1-pyrophosphate (PRPP) and then converted to AMP. Ribose is found in the normal diet only in very low amounts, and is synthesized within the body by the pentose phosphate pathway. In the de novo synthetic pathway, ribose is phosphorylated to PRPP, and condensed with adenine to form the intermediate adenosine monophosphate (AMP.) AMP is further phosphorylated via high energy bonds to form adenosine diphosphate (ADP) and ATP. During energy consumption, ATP loses one high energy bond to form ADP, which can be hydrolyzed to AMP. AMP and its metabolites adenine, hypoxanthine and inosine are freely diffusible from the muscle cell and may not be available for resynthesis to ATP via the salvage pathway.

In U.S. Pat. No. 4,719,201, it is disclosed that when ATP is hydrolyzed to AMP in cardiac muscle during ischemia, the AMP is further metabolized to adenosine, inosine and hypoxanthine, which are lost from the cell upon reperfusion. In the absence of AMP, rephosphorylation to ADP and ATP cannot take place. Since the precursors were washed from the cell, the nucleotide salvage pathway is not available to replenish ATP levels. It is disclosed that when ribose is administered via intravenous perfusion into a heart recovering from ischemia, recovery of ATP levels is enhanced.

The availability of PRPP appears to control the activity of both the salvage and de novo pathways, as well as the direct conversion of adenine to ATP. Production of PRPP from glucose via the pentose phosphate pathway appears to be limited by the enzyme glucose-6-phosphate dehydrogenase (G6PDH). Glucose is converted by enzymes such as G6PDH to ribose-5-phosphate and further phosphorylated to PRPP, which augments the de novo and salvage pathways, as well as the utilization of adenine. The addition of ribose bypasses this rate limiting enzymatic step.

Many conditions produce hypoxia. Such conditions include acute or chronic ischemia when blood flow to the tissue is reduced due to coronary artery disease or peripheral vascular disease where the artery is partially blocked by atherosclerotic plaques. Transient hypoxia frequently occurs in individuals undergoing anesthesia and/or surgical procedures in which blood flow to a tissue is temporarily interrupted. Peripheral vascular disease can be mimicked in intermittent claudication where temporary arterial spasm causes similar symptoms. Finally, persons encountering high altitudes may become hypoxic.

Thus, a continuing need exists for methods to raise the hypoxic threshold of cardiac and skeletal muscle.

SUMMARY OF THE INVENTION

The present invention provides compositions for, and methods to raise the hypoxic threshold in a mammal. It is believed that the present compositions and methods allow mammals to tolerate situations in which, absent the present compositions and methods, the mammal would experience the onset of symptoms and consequences of hypoxia. The preferrred compositions include D-Ribose alone or, optionally, in combination with vasodilators and/or inotropic agents in pharmaceutically acceptable carriers. Hypoxia may be chronic, as in mammals with congestive heart failure, coronary artery disease or peripheral vascular disease. Hypoxia may also be transient, as in mammals undergoing anesthesia and surgical procedures, experiencing high altitudes, or exposed to toxic substances that interfere with oxygen utilization.

It is here shown that the administration of ribose will raise the hypoxic threshold of a mammal such as a human or domestic animal, thereby enabling such mammals to better tolerate the situation causing hypoxia. It is further disclosed that in mammals in which the hypoxia is caused by reduced blood flow due to arterial occlusion or spasm, the administration of ribose plus a vasodilator will enhance the raising of the hypoxic threshold.

DETAILED DESCRIPTION OF THE INVENTION

The present invention provides a method of raising the hypoxic threshold of a mammal such as a human or domestic animal, by the administration, i.e., oral, intravenous or peritoneal administration of and effective amount of ribose to said mammal. The invention also provides provides ribose-containing compositions that enhance the delivery of ribose to target tissue and are therefore especially beneficial to mammals experiencing hypoxia.

For the purpose of describing this invention, the following terms have the following meanings:
1. "Ribose" means a monosaccharide, including but not limited to, ribose, and any 5-carbon precursor of ribose, D-ribose, ribulose, xylitol and xylulose.

2. "Vasodilator" includes any substance that causes dilation of blood vessels, including but not limited to, adenine, hydralazine, arginine, nitroglycerine or analogs thereof, administered alone or in combination, transdermally or orally, or physical agents such as hot compresses, heating pads or ultrasound administration.
3. "Inotropic agent" includes any substance which increases the stroke volume and cardiac output of the heart, including but not limited to, dobutamine, arbutamine, dopamine, amrinone and milrinone, and anlaogs thereof, alone or in combinaton.
4. "Hypoxia" means any state in which the tissue oxygen saturation is reduced to a less than optimal level. Hypoxia includes anoxia, ischemia and poisoning with toxic agents such as carbon monoxide and cyanide which interfere with oxygen utilization. Hypoxia may be chronic as in congestive heart failure, coronary artery disease, peripheral vascular disease or pulmonary dysfunction, or transient as in anesthesia, surgical procedures or exposure to high altitudes.
5. "Hypoxic threshold" is that basal level where oxygen saturation of tissues less than optimal. A raised hypoxic threshold increases tolerance to situations which would otherwise result in hypoxia.
6. "Ischemia" is that state of hypoxia caused by reduced circulation of blood to tissue.

In patients with ischemic heart disease, regions of the heart may be poorly perfused, dysfunctional, but still viable. Myocardial ischemia limits blood flow and therefore the available supply of oxygen. This limited availability of oxygen affects oxidative metabolism, which ultimately negatively affects the production of adenosine triphosphate (ATP), essential for maintenance of contractility and cellular integrity. Varied states of ischemia exist. However, either transient or chronic ischemia may result in partial reduction of myocardial ATP with subsequent impairment of contractile function, which can lead to heart failure but not cell death.

Therapeutic intervention is variable and must be tailored to each patient. Non-surgical therapies may offer a primary mode of treatment. The first line of action includes angiotensin-converting inhibitors, digoxin and diuretics. So-called inotropic agents such as dobutamine, arbutamine, dopamine, amrinone and milronine, which increase stroke volume and cardiac output, have been universally used for treatment of cardiac dysfunction, which can be manifested by edema, dyspnea, pulmonary congestion and organ hypoperfusion. Many previous studies have investigated the use of ribose in healthy animals such as dogs, rats and swine that have been subjected to ischemic insult. While such studies maysuggest therapies for humans with cardiovascular disease, subsequent human clinical studies often fail to support these suggestions.

Many patients suffering from "silent" cardiovascular disease, that is, such patients are unaware of their condition of chronic hypoxia. The treadmill test has been extensively used to raise the oxygen demand of the heart and uncover the low hypoxic threshold. However, treadmill testing may not be the test of choice in all situations. Dobutamine has been found particularly useful for simulating exercise in patients with coronary artery disease. The infusion of dobutamine produces a stressful myocardial condition similar to that produced by exercise, while the patient is in a controlled hospital setting, with intravenous infusion, in which intervention is readily available. It is theorized that dobutamine increases myocardial stroke volume and cardiac output while reducing ventricular volume and mitral regurgitation due to its vasodilating effects. Because of these multiple effects, dobutamine has been investigated extensively as an agent to increase sensitivity in identifying segmental wall motion activity by echocardiography.

In co-pending patent application Ser. No. 09/290,789 (the "'789 Application"), the teaching of which is hereby incorporated by reference, it is disclosed that administration of D-ribose increases the energy level of mammals by stimulating the synthesis of ATP. Examples therein show that ATP levels in the skeletal muscle of healthy mammals under normal conditions of oxygen availability increase upon ribose administration and that the increase is correlated with an increase in performance and activity levels. It is also shown that administration of D-Ribose provides some benefit even to patients with coronary artery disease.

The present invention is based on the discovery that administration of ribose can also increase the tolerance of tissue to low oxygen availability, that is, to hypoxia. Energy and oxygen availability can each independently influence tissue integrity and function. Although ribose has been shown to enhance energy levels under conditions of normal oxygen availability, the present invention surprisingly shows that when ribose is present, tissue can endure low oxygen availability while still maintaining normal function, without being subjected to the deleterious effects due to low oxygen. Even if energy is available in sufficient quantities, but oxygen is low, adverse effects may still occur in the hypoxic tissue. These effects include pH changes, imbalance in intermediate metabolites and the like. In other words, ribose ameliorates the effects of hypoxia, that is, it raises the hypoxic threshold.

The advantages of ribose in raising the hypoxic threshold may not be readily available to mammals with poor circulation and that therefore the benefits shown in the '789 Application may fall far short of optimal. The present method also contemplates the use of vasodilators and/or inotropic agents ("inotrops") to increase the delivery of ribose to tissue in order that mammals may experience the maximum benefit from ribose administration.

It has been investigated and is here disclosed that the beneficial effects of D-ribose, in the presence of a vasodilator, provides overall stabilization and/or improvement in myocardial function in patients with severe cardiovascular disease. The effect of D-Ribose on heart wall motion seen on echocardiographic examination was studied in various populations suspected of having stunned or hibernating myocardium, as is more fully disclosed in co-pending patent application, Ser. No. 09/405,462 entitled EFFECT OF RIBOSE ON THE ISOTROPIC RESPONSE TO DOBUTAMINE, which was filed on the same day as this application. Upon infusion of high levels of dobutamine, at a dosage sufficient to simulates exercise stress, ribose was shown to raise the hypoxic threshold and enabled patients to tolerate high levels of dobutamine. It is believed that co-administration of D-ribose and a vasodilator will enhance myocardial energy levels in cardiovascular patients and will raise their hypoxic threshold. This, in turn, will improve their clinical status before, during and after revascularization or heart transplant, and enhance the treatment of cardiovascular disease or end-stage heart disease or failure. It is further believed that perfusion of a donor heart with D-Ribose before removal from the donor and during transport, will prolong the period during which the heart is suitable for transplant.

Even persons free of disease occasionally experience transient situations of hypoxia. Such situations include exposure to high altitudes, anaesthesia, tachycardia, surgical procedures that temporarily interrupt blood flow, and poisoning with agents such as iron carbonyl, carbon monoxide and cyanide that interfere with oxygen utilization. Such persons would benefit by the raising of the hypoxic threshold.

The present method comprises the administration of an effective amount of D-Ribose for an adequate period of time to raise the hypoxic threshold in mammals. This method also comprises the administration of D-Ribose in combination with a vasodilator to patients subject to acute or chronic hypoxia, accompanied by poor circulation, in adequate amounts for a period of time to raise the hypoxic threshold. This method provides the combined effects of D-Ribose and mid- or high-dose dobutamine admionistration so as to reduce or eliminate the deleterious effects of hypoxia. This invention provides D-ribose to patients already receiving dobutamine as part of their post-operative management following a revascularization procedure, in order to improve their clinical outcome.

DETAILED DESCRIPTION OF THE INVENTION

Myocardial hibernation and stunning define conditions in which tissue viability may be present but is hindered in the presence of reduced regional or global blood flow. The phenomenon of hibernating and stunned myocardium has been the subject of increasing interest with recognition that function may improve in these regions after restoration of adequate blood supply or treatment with newly available therapies such as the Batista procedure, in which the diastolic volume of the ventricle is surgically reduced by removal of non-viable or poorly viable tissue. The resulting ejection efficiency of the ventricle is improved with the patient usually experiencing a clinical benefit.

Among the techniques used to distinguish non-viable from viable myocardium, echocardiography is commonly used because of its direct measurement of contractile function, which is thought to be a better predictive indicium than blood-flow tracing with radionuclides. Myocardial stress induced by dobutamine infusion increases the sensitivity of echocardiography. However, the sensitivity of this technique for detection of viable myocardium may be limited in the presence of severe coronary artery disease. Although sensitivity is correlated to mid- or high doses of dobutamine, that is, 10 to 40 $\mu$g/kg/min, high doses cause ischemia and distress in these vascularly compromised patients. It is herein disclosed that when ischemia is induced with mid- or high-dose dobutamine, D-Ribose raises the hypoxic threshold. From these results, it can be predicted that the hypoxic threshold of mammals in other situations that result in the symptoms of ischemia, will likewise be raised by the administration of ribose. In this example, ribose was administered intravenously. However, it is well known that ribose is readily absorbed from the gastrointestinal tract and the peritoneal lining. Therefore, the route of administration may be determined by convenience. Ideally, oral administration of ribose is the preferred route. If the patient is attached to an intravenous line, it may be more convenient to add ribose to the infusate. If the patient is unable, unwilling, or uncooperative enough to tolerate oral or intravenous administration, peritoneal infusion can be used quickly and effectively.

Coronary artery bypass grafting (CABG) has become a routine procedure. During this procedure, blood flow is restored to regions of the heart served by stenotic coronary arteries. Identification of those areas that are hibernating or stunned and identifying the non-viable segments aids the surgeon in revascularizing those regions that are most capable of being revived and improved with reperfusion.

Peripheral vascular disease (PVD) is caused by stenoses of the peripheral arteries, leading to hypoxia of the skeletal muscles, especially during exercise. Patients suffering from PVD are frequently unable to walk for a distance before experiencing severe pain and fatigue. Raising the hypoxic threshold by the administration of ribose, preferably with a vasodilator, can reduce or eliminate these symptoms.

Various methods of revascularization may be considered by the medical personnel and subsequently offered to the patient. Ischemia may be viewed in the disease state as either acute or chronic, and decisions made accordingly. Table I summarizes the decision grid.

TABLE I

| Choice of Therapy | |
|---|---|
| ACUTE ISCHEMIA (myocardial infarction or coronary arteriospasm) | CHRONIC ISCHEMIA (coronary artery occlusion) |
| Coronary Artery Disease | |
| CABG coronary balloon angioplasty coronary artery atherectomy | CABG coronary balloon angioplasty coronary artery atherectomy transmyocardial revascularization heart transplant |
| Peripheral Vascular Disease | |
| embolectomy | peripheral vessel balloon angioplasty peripheral vessel bypass peripheral vessel atherectomy |

Each treatment carries its own risks and benefits. For example, angioplasty has a lower rate of long-term success than CABG due to the tendency of the vessel to re-occlude ("restenosis"), but because it is a simpler procedure with lower risks, it will be often indicated as a first course of action, when the patient has an amenable lesion. However, not all patients carry the same preoperative risk for each procedure. If the heart contains large areas of non-viable tissue with severely decreased myocardial performance, a heart transplant rather than CABG may be the patient's only alternative. Regardless of the surgical therapy chosen, preconditioning with oral and/or IV D-Ribose, preferably in conjunction with vasodilator administration, decreases the risk to the patient by raising the hypoxic threshold. Preoperative, operative and postoperative risks, which include death, infarction and myocardial dysfunction are lessened.

Just as the recipient patient benefits from the administration of D-Ribose, the donor heart used in transplantation can benefit from the use of D-Ribose. By administration of D-Ribose, the donor heart will show higher maintenance of energy levels and function during preservation and following revascularization. It is expected that this extended maintenance of viability will allow the ischemic period of preservation to be extended, so that more donor hearts will be available and optimal matching of donor and recipient may occur across a wider geographic area.

In the '789 Application, it is disclosed that healthy mammals show an increase in ATP following administration of D-Ribose and that humans with CAD show improvement in clinical condition on oral administration of D-Ribose. The use of dobutamine for echocardiographic diagnosis of stunned or hibernating myocardium clearly indicates that concomitant administration of a vasodilator with D-Ribose further enhances the ribose effect, enabling the patient to tolerate stress of a degree that would, in the absence of either ribose or vasodilator, cause symptoms of hypoxia. Without being bound by theory, it would seem that ribose alone is sufficient to raise the hypoxic threshold, but that in CAD patients, arterial stenosis (es) may impede the delivery of ribose to the muscle tissue. Therefore, it is apparent that the administration of a vasodilator with D-Ribose will improve the tolerance to hypoxia in a CAD patient.

The references identified in the specification are incorporated herein by reference to the extent that they supplement, explain, provide background for, or teach the methodology, techniques and/or compositions employed herein.

The following examples are included to demonstrate preferred embodiments of the invention. In each example, D-Ribose is disclosed as the preferred embodiment. However, it is known in the art that certain pentoses such as xylitol and ribulose are readily converted to D-Ribose in vivo. Therefore, the term "D-Ribose" is intended to include such precursors of D-Ribose. It should be appreciated by those skilled in the art that the techniques and dosages disclosed in the examples that follow represent techniques and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1
Effect of D-ribose on Nucleotide Salvage in Resting Rat Muscle

It has been theorized but not objectively shown that ribose, via PRPP synthesis, increases the rate of ATP synthesis via the nucleotide salvage pathway. However, nothing is known about the total adenine nucleotide (TAN) or ribose levels in the resting muscle and therefore, it is possible that the synthetic enzyme pathway is already saturated and that administration of ribose does not increase ATP levels in normal, non-ischemic skeletal muscle. In order to demonstrate the effect of ribose on the pathway, plantaris complex muscles of healthy adult male Sprague-Dawley rats were surgically exposed and perfused with reconstituted blood perfusion medium containing amino acids, mM glucose and 100 µU of bovine insulin/ml. The muscle was perfused with reconstituted blood medium at ~40 ml/min, providing tissue perfusion of approximately 0.65 ml/min. Varying concentrations of D-ribose were added to the perfusate to bring the concentration to 0.156 mM, 0.5 mM, 1.58 mM, 5.0 mM and 15.0 mM. The muscle was perfused for 30 minutes. A minimum of two rats was used for analysis at each dose of ribose tested.

Following perfusion, muscle sections were quickly dissected from the limb and freeze-clamped with aluminum tongs chilled in liquid nitrogen. Muscle sections were lyophilized and reconstituted in distilled water for subsequent separation of adenine nucleotides by reverse-phase high pressure liquid chromatography. Results are expressed as salvage of adenine (i.e., formation of ATP) in nanomoles salvaged per gram wet weight of muscle per hour (nM/gm/hr).

TABLE II

Ribose Skeletal Muscle Dose-Response Kinetics

| mM Ribose | Observed | Saturation Kinetics with Base |
|---|---|---|
| 0.000 | 48.6 | |
| 0.158 | 113.0 | 85.82 |
| 0.500 | 110.0 | 118.68 |
| 1.000 | | 154.12 |
| 1.580 | 188.5 | 183.51 |
| 2.000 | | 199.74 |
| 2.500 | | 215.29 |
| 3.000 | | 227.85 |
| 5.000 | 250.0 | 260.68 |
| 15.000 | 315.5 | 310.37 |

Figure 1:
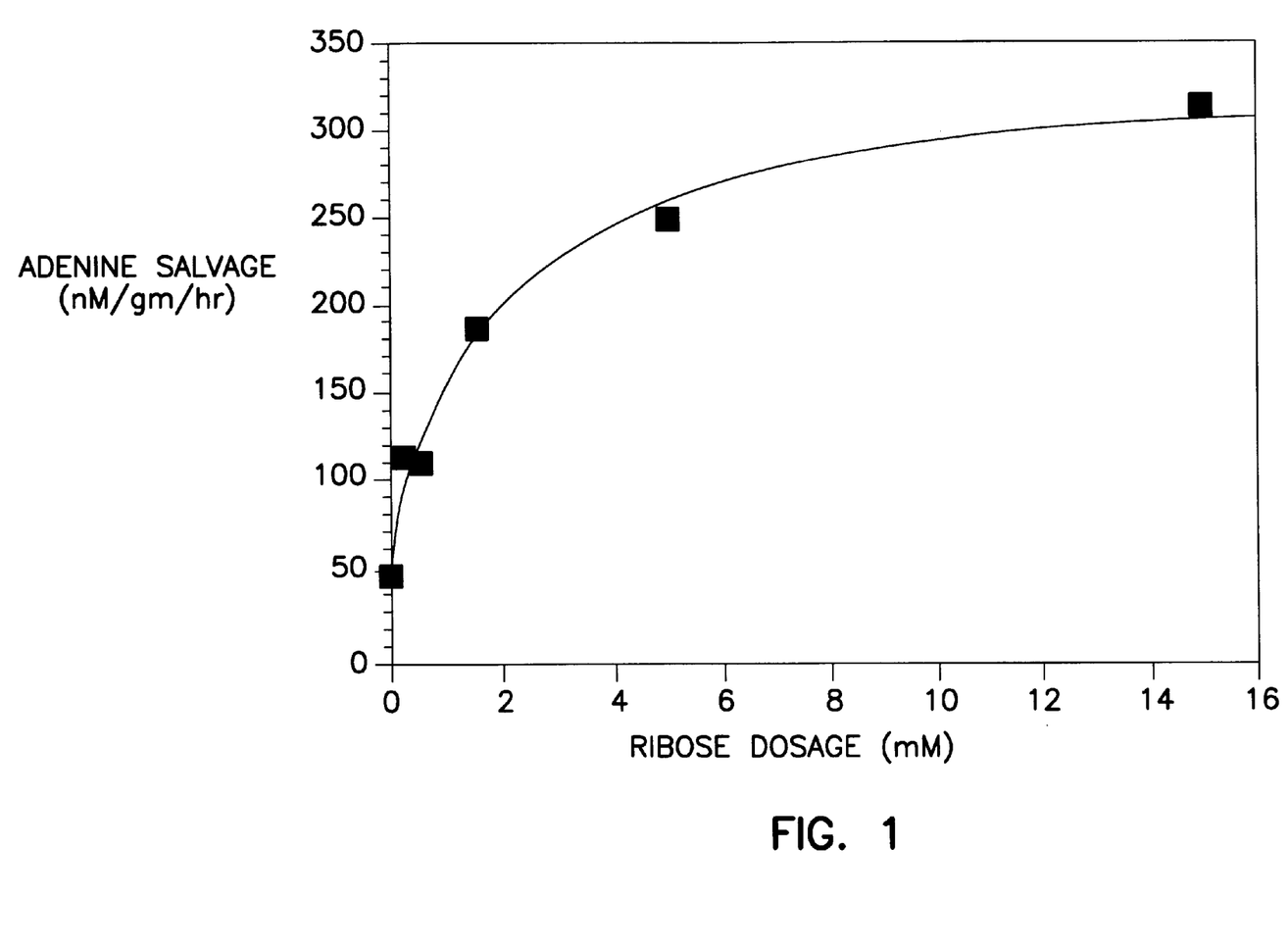
FIG. 1 shows the dose response of the adenine salvage pathway in normal adult rats to the administration of ribose.

As is shown in FIG. 1 and Table II, adenine salvage at zero millimolar (mM) ribose is less than 50 nM/gm/hr and doubles with administration of 0.158 mM ribose. At 5 mM ribose, the rate of ATP synthesis reaches 250 nM/gm/hr. These results show that normal, healthy muscle has low baseline levels of ribose and nucleotide salvage capability, which can be increased by the administration of ribose.

EXAMPLE 2
Increased Exercise Capacity in Normal Subjects

Four healthy, fit subjects in the age range 24 to 26 years of age were tested. The group was selected to be homogeneous regarding fitness level, gender and mean age with no known metabolic, neuronal, endocrine or cardiopulmonary disorders. All were capable of or had experience with cycling. The study protocol included four phases: (1) an initial baseline phase consisting of no exercise session; (2) a loading phase including three days of administration of either D-ribose or placebo (glucose) three times per day; (3) a training phase of three days employing exercise sessions characterized by serial (N=6) bouts of short (10 second) high-intensity cycle sprints at 7% body mass resistance with 50 second rest periods between sprints twice per day (morning and afternoon), and (4) a recovery phase for a period of 48 hours after the final training session. FIG. 1 is a diagram of a single cycle sprint bout.

Muscle biopsies (MB) were performed on the vastis lateralis muscle using both legs in order to evenly distribute and minimize sampling and possible muscle soreness per leg due to the biopsy itself. The first MB was collected at rest at the beginning of the study to establish a baseline and immediately after the first training session of day 0 or the first phase. During the loading phase, no MB was taken. Muscle Biposies were taken following the final training session and after 48 hours of recovery.

Two subjects were randomly selected for inclusion into the placebo or ribose group. Ribose or glucose was administered orally in a 250 ml iso-osmotic solution containing 10.0 grams of either ribose or placebo three times per day for three days preceding training (loading phase) and for three days during training (training phase). One-half liter isotonic electrolyte solution was given immediately post exercise and again 30 minutes later to avoid dehydration.

The concentration of the following analytes was determined in the MB samples: ATP, ADP, AMP, IMP (inosine monophosphate), TAN (total adenine nucleotides), creatine phosphate and creatine.

TABLE III

Ribose Athlete Study
Mean Power Per Kilogram (Watts)

| Subject | 1 | 2 | 3 | 4 | 5 | 6 | Average | |
|---|---|---|---|---|---|---|---|---|
| 1P | 6.0 | 6.7 | 7.3 | 7.4 | 7.3 | 7.5 | 7.0 | |
| 2R | 6.9 | 7.5 | 7.8 | 7.6 | 7.9 | 7.4 | 7.5 | |
| 3R | 8.7 | 9.2 | 9.1 | 9.0 | 8.5 | 8.2 | 8.8 | |
| 4P | 7.5 | 8.0 | 7.7 | 8.7 | 8.0 | 7.6 | 7.9 | |
| Placebo | 6.8 | 7.4 | 7.5 | 8.0 | 7.6 | 7.6 | 7.6 | 100.0% |
| Ribose | 7.8 | 8.4 | 8.5 | 8.3 | 8.2 | 7.8 | 8.2 | 109.0% |

TABLE IV

Ribose Athlete Study
Peak Power Per Kilogram (Watts)

| Subject | 1 | 2 | 3 | 4 | 5 | 6 | Average | |
|---|---|---|---|---|---|---|---|---|
| 1P | 6.8 | 7.9 | 8.6 | 8.6 | 8.3 | 9.0 | 8.2 | |
| 2R | 7.9 | 8.8 | 9.2 | 9.0 | 9.4 | 8.7 | 8.8 | |
| 3R | 9.8 | 10.6 | 10.7 | 10.7 | 10.1 | 9.9 | 10.3 | |
| 4P | 7.7 | 8.6 | 8.7 | 9.4 | 8.8 | 9.0 | 8.7 | |
| Placebo | 7.7 | 8.6 | 8.7 | 9.4 | 8.8 | 9.0 | 8.7 | 100.0% |
| Ribose | 8.9 | 9.7 | 10.0 | 9.9 | 9.8 | 9.3 | 9.6 | 109.9% |

TABLE V

Ribose Athlete Study
Total Power Per Kilogram

| Subject | 1 | 2 | 3 | 4 | 5 | 6 | Average | |
|---|---|---|---|---|---|---|---|---|
| 1P | 59.1 | 67.0 | 72.7 | 73.3 | 72.5 | 74.2 | 69.8 | |
| 2R | 71.9 | 74.7 | 77.1 | 75.6 | 78.1 | 73.4 | 75.1 | |
| 3R | 86.8 | 91.9 | 91.3 | 90.0 | 85.4 | 82.5 | 88.0 | |
| 4P | 74.5 | 80.3 | 76.8 | 87.4 | 80.0 | 76.4 | 79.2 | |
| Placebo | 66.8 | 73.6 | 74.8 | 80.4 | 76.3 | 75.3 | 74.5 | 100.0% |
| Ribose | 79.3 | 83.3 | 84.2 | 82.8 | 81.8 | 77.9 | 81.6 | 109.5% |

Figure 2:
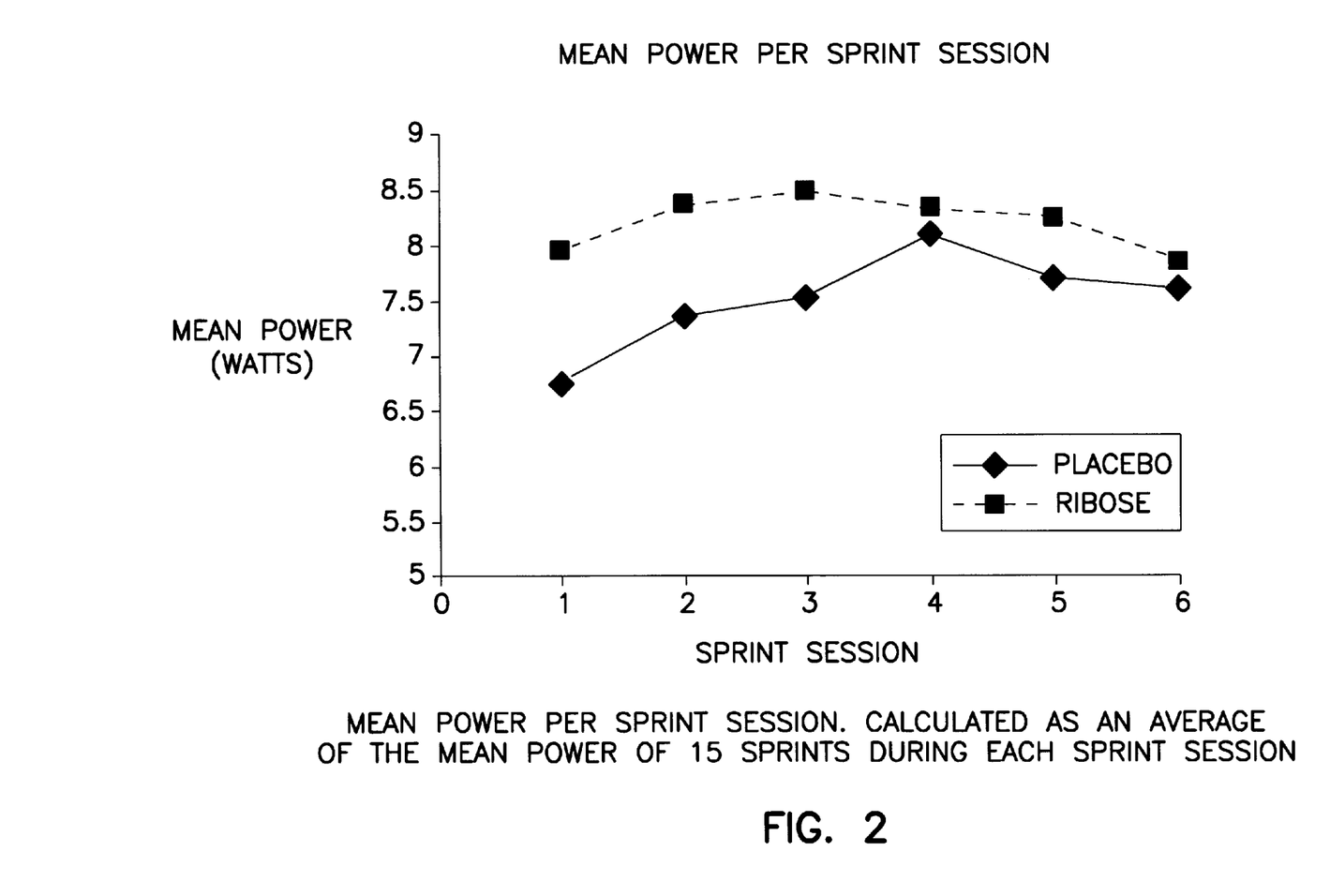
FIG. 2 shows the mean power output per sprint session of normal adult humans, following administration of ribose or placebo, as measured on an exercycle.
Figure 3:
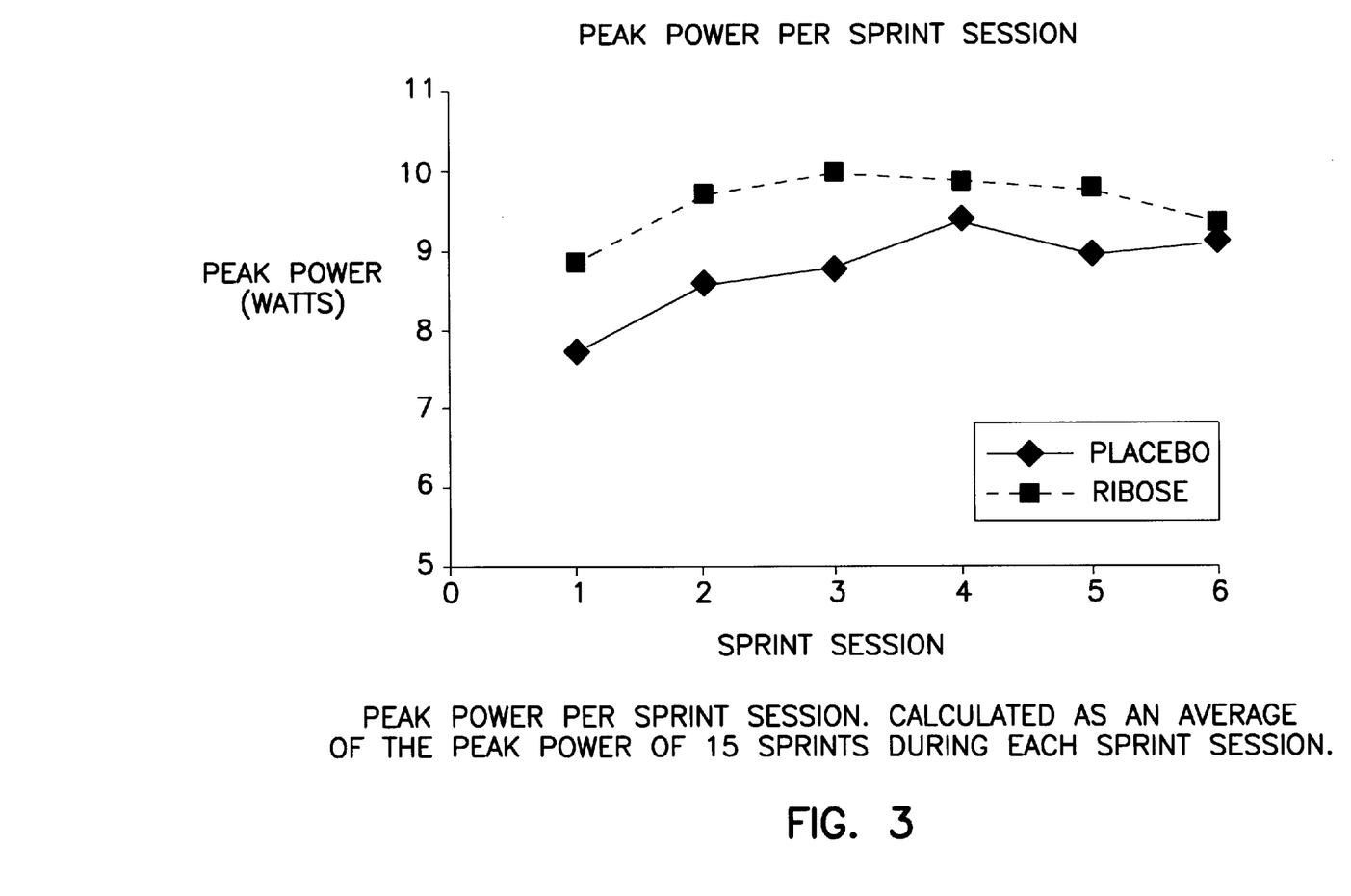
FIG. 3 shows the peak power output per sprint session of normal adult humans, following administration of ribose or placebo, as measured on an exercycle.

As can be seen from Tables III to V and FIGS. 2 and 3, administration of ribose increased performance by 9%.

The improvement in performance is reflected in the ATP levels in the muscle biopsies. As shown in Table VI, the subjects preloading with ribose for three days began the training phase with higher levels of ATP, which declined significantly more than that of the placebo group after the sprint bouts, indicating that ATP was being utilized more efficiently. Recovery of the ribose group at 48 hours was 82% of the initial level, compared to 78% in the placebo group.

TABLE VI

Mean ATP Values (mmol/kg dw)

| Group | Pre | Post | Recovery | Recovery % of Pre | Change Pre-Post | Change Post-Rec |
|---|---|---|---|---|---|---|
| Placebo | 23.60 | 20.05 | 18.30 | 78% | −3.55 | −1.75 |
| Ribose | 25.33 | 13.90 | 20.80 | 82% | −11.43 | 6.90 |

EXAMPLE 3
Use of D-Ribose Plus Dobutamine
A. Echocardiography

A single-center, randomized, double-blind placebo-controlled clinical trial was carried out to evaluate the safety and efficacy of D-Ribose on myocardial wall motion during echocardiographic examination in patients suspected of having stunned or hibernating myocardium.

Patients Included:
ages 18 or older, male or female
stable resting wall motion abnormalities noted on baseline echocardiography, defined as at least two segments with abnormal function.
at least five days from a major cardiac event such as myocardial infarction or unstable angina
no known allergies or contraindications to D-Ribose or dobutamine
stable medical regimen of vasoactive medications
known coronary artery disease (CAD) discovered by cardiac catheterization, myocardial infarction or positive stress test

OR patients with high index of suspicion for CAD provided they have a resting wall abnormality on ECHO
for females of child-bearing potential, a negative pregnancy test
signed informed consent approved by an Institutional Review Board
Patients excluded:
diabetes mellitus requiring insulin or an oral hypoglycemic agent
inability to sign consent form
history of non-ischemic cardiomyopathy
clinically significant liver or renal disease in the judgment of the investigator
advanced valvular heart disease in the judgment of the investigator Patients were randomized into placebo and ribose groups according to a computer generated randomization schedule. The identity of the contents was blinded to the investigator. Patients were identified by initials. The selected study population was comprised of 25 patients (22 men and 3 women) with a mean age of 57+/−11 years. All had reduced left ventricular systolic function (mean ejection fraction 30+/−8%, range 18 to 48%). Twenty-two patients (88%) had prior myocardial infarction and only one subject was evaluated after recent (<4 weeks) infarction. Nineteen patients (76%) had stable angina pectoris and 21 (84%) were receiving one or more medications to treat ischemia (nitrates (21), beta-antagonists (9), calcium channel antagonists (9)). Coronary artery disease (>=50% diameter stenosis) was documented by angiography in 22 patients. Of the 21 who had recent studies, 12 had three-vessel, 8 had two-vessel and one had single vessel disease. Subjects were admitted to the hospital on the morning of study day 1 after an 8 hour fast. After a limited physical examination, a baseline (AM) echocardiogram was obtained. Following the imaging study, continuous monitoring of the heart rhythm was initiated.

After completion of the baseline echocardiography, intravenous infusion of test agent (D-Ribose or placebo) at a set infusion, along with an infusion of 5% glucose in water (D5W) at 100 ml/hour as a maintenance fluid was initiated. D-Ribose, 10% in water at 180 mg/kg/hour, or placebo D5W at 1.8 mg/kg/hour, were given as sterile, pyrogen-free solutions. After the test agent had been administered for one, two, three or four hours, a resting echocardiogram was obtained. At completion of this rest period, dobutamine was infused. Dobutamine hydrochloride (Dobutrex® solution, Eli Lilly, Indianapolis) was mixed in D5W (5% dextrose in water), giving a concentration of 1.0 mg/ml. During echocardiography, dobutamine was administered at an initial dose of 5 μg/kg/minute for three minutes. The dose of dobutamine was then increased to 10 μg/kg/min and infused for three minutes. Echocardiograms were obtained at the low dose stages and at peak stage. Every three minutes the concentration of dobutamine was increased by 10 μg/kg/minute increments until the standard endpoint was reached. The standard endpoint was set to be ≧2 mm ST-segment depression on ECG; significant side effects or arrhythmias; achievement of 85% of the age-predicted maximal heart rate; a systolic blood pressure >250 mm Hg, a significant fall in systolic blood pressure or a maximal dose of 50 μg/kg/minute.

Post-infusion images were recorded approximately eight minutes after discontinuation of dobutamine. Upon completion of imaging, the test article infusion was terminated. Subjects were observed overnight and on Day 2 were crossed over to the alternate test article. Study protocols on Day 2 were identical to those of Day 1.

B. Echocardiographic Analysis

Baseline (AM) and PM two-dimensional echocardiograms and any post-revascularization studies were performed using an Advanced Technology Laboratories UM9 HDI (Bothell, Wash.) with a 3.0 MHZ phased array transducer and a Hewlett Packard Sonos 1500 (Andover, Mass.) with a 2.5 MHZ phased array transducer. Parasternal long and short-axis and apical two and four-chamber images were recorded on 0.5 inch videotape and digitally stored on floppy discs using a Nova MicroSonics DCR or Colorvue system (Mahwah, N.J.). End-diastolic and systolic images were acquired on line at 67 msec intervals.

The Day 1 and Day 2 AM and PM echocardiograms for each subject were transferred from floppy disk to a customized image network where each subject's images were archived only by hospital number. The images were retrieved from the network and analyzed using the Indiana University Off-line Revue System. Once retrieved, the images were rearranged in computer memory to display AM and PM images side by side for each echocardiogram view. Two blinded investigators rendered a consensus interpretation of regional wall motion in 16 left ventricular segments. Wall motion was graded as: (1) normal; (2) mildly hypokinetic with <5 mm inward systolic motion; (2.5) severely hypokinetic with minimal inward systolic motion and wall thickening; (3) akinetic with an absence of inward motion and wall thickening; (4) dyskinetic with paradoxical outward motion. A global wall motion score was derived for each echocardiogram (sum of individual segment scores per number of segments scored.)

The Day 1 and Day 2 dobutamine echocardiograms comprised of resting, 5, 10 μg/kg/minute, and peak dose images were stored and reviewed using the procedures and equipment previously described for the AM and PM images, except that side by side comparison was not performed. Using the previously described scoring system, regional wall motion was graded by consensus by two blinded investigators. Hyperdynamic wall motion during dobutamine infusion was scored as one normal wall motion. A one grade improvement of wall motion during dobutamine infusion was considered significant. Global wall motion scores were derived for each stage of the dobutamine echocardiogram.

During low-dose dobutamine, wall motion improved in more segments on D-Ribose than placebo (65 segments v. 48 segments ). Stress-induced ischemic abnormalities occurred in more segments on placebo than on ribose (43 segments v. 31). Stress-induced abnormalities occurred in more patients on placebo than on ribose (71% v. 46%).

Eleven patients subsequently underwent CABG after completion of Study Day 2. At least one echocardiogram was obtained postoperatively in each of these subjects. Regional wall motion was compared between the follow-up echocardiogram and the Day 1 AM study by two blinded investigators. A single, blinded investigator made determinations of ejection fraction on the AM, PM, dobutamine and any post-revascularization echocardiograms using the four-chamber view and the Simpson's method. As shown in Table VII, the accuracy of dobutamine plus D-Ribose in identifying patients with increase in ejection fraction (EF) after surgery greater than or equal to 5% was 82% compared to 45% of placebo controls.

TABLE VII

Improvement of Ejection Fraction Following CABG

| | Analysis 1: EF Increase ≧ 5% | | Analysis 2: EF Increase ≧ 10% | |
|---|---|---|---|---|
| | Ribose | Placebo | Ribose | Placebo |
| Sensitivity | 89% (8/9) | 56% (5/9) | 57% (4/7) | 29% (2/7) |
| Specificity | 50 (1/2) | 0 (0/2) | 100 (4/4) | 25 (1/4) |
| Accuracy | 82 (9/11) | 45 (5/11) | 73 (8/11) | 27 (3/11) |

EXAMPLE 4

Relief of Exercise Induced Angina in Patients with CAD

A sixty-eight year old male patient with a history of coronary artery disease, status post triple coronary artery bypass, experienced exercise induced angina. His present medications are: enalapril (an angiotensin converting enzyme inhibitor), carvedilol (a β blocking agent), nitroglycerine patch and nitroglycerine tablets sublingual as needed. The most recent coronary angiogram revealed advancement of his coronary artery disease with total occlusion of one of the bypass grafts. The patient performed poorly on two stress tests. His exercise regimen consisted of a daily walk.

Due to the development of angina caused by hypoxia, the patient was able to walk less than one mile per day, at which point he took sublingual nitroglycerine. The patient was given oral D-ribose dissolved in about 250 cc. of water. Over a six-month period, the patient received intermittent doses of 5–10 grams per day of D-ribose. Post ribose administration, the patient was able to increase his exercise tolerance to two miles per day without any supplementation of oral nitroglycerine. When the ribose was discontinued, his pre-ribose, anginal-inducing exercise state recurred, which necessitated the use of supplemental oral nitroglycerine. Resumption of oral ribose allowed the patient to walk two miles per day, without angina or the need for nitroglycerine. His subjective evaluation of the ribose treatment is there is "much less angina pain. I feel better, have more energy and can be more active without pain or pills [nitrogycerine]."

The patient will be placed on a regimen of ribose ingestion followed by low-dose nitroglycerine within 30 minutes, at least one hour before exercise, in order to obtain the increased benefits of preloading with ribose, as is seen in Example 3.

EXAMPLE 5

Improved Treadmill Test Performance

A sixty-year old male patient with stable coronary artery disease was observed to show a greater than fifty percent occlusion of more than one epicardial coronary artery and stable angina. The patient was tested for treadmill performance. After two baseline treadmill tests, following the Bruce protocol, he received orally administered D-ribose (40 gm in three divided doses daily) for three days and completed a third treadmill test. At each time, the test was to be stopped when a) the patient exhibited ST segment depression of 1 mm or more in the ECG tracing; b) when the patient complained of angina or c) when the patient stopped due to dyspnea or fatigue. In each test, this patient concluded the test due to shortness of breath, but experienced no angina.

As can be seen from Table VIII, the administration of D-ribose for three days before the final treadmill test increased energy and heart function as measured by decrease in rate-pressure product at each stage of testing, including rest (zero time). It is generally accepted that the product of heart rate and systemic pressure is a measure of myocardial function and energy level, with lower numbers indicating better myocardial function. As a result of the administration of ribose, average tolerated time on the treadmill increased. In addition to the objective measure of efficacy, the patient subjectively reported feeling more energetic during ribose administration.

| Time | Baseline 1 | Baseline 2 | Average | Test | % Change |
|---|---|---|---|---|---|
| 0 (rest) | 11,088 | 9,272 | 10,180 | 9,177 | −9.55% |
| 3 minutes | 17,574 | 13,468 | 15,521 | 15,272 | −1.60% |
| 6 minutes | 26,500 | 22,344 | 24,422 | 20,592 | −15.68% |
| 9 minutes | 33,396 | 29,526 | 31,461 | 25,356 | −9.87% |
| Tolerated time, sec. | 483.00 | 545.00 | 514.00 | 540.00 | 5.06% |

In the Bruce protocol, the treadmill speed in increased in three minute increments from 1.7 to 6.0 miles per hour, while the slope is increased from 10 to 22%.

It is expected that these results will be further improved if the patient also uses a vasodilator as per example 4.

EXAMPLE 6
D-Ribose and Vasodilating Agents

Results reported by Angello show that ribose unmasked ischemic myocardial tissue in the healthy swine heart. (U.S. Pat. No. 4,824,660) It should be pointed out that most of the prior studies on the effect of ribose were performed on healthy animals such as dogs and swine. For example, Foker (U.S. Pat. No. 4,719,201) found that when healthy dogs were made globally ischemic by cross-clamping the ascending aorta for 20 minutes, the infusion of 5% ribose allowed faster recovery of ATP levels. Likewise, Angello found that ribose, in the absence of a vasodilating agent, improved blood flow in the stunned heart of healthy swine, while Sawada found slight beneficial effect of ribose before the co-administration of dobutamine. The difference between the results of Angello's swine study and those found here may be be due to the poor circulation in the patients in this study which impedes the delivery of ribose to the tissue.

Therefore, ribose given with any of the known vasodilators, such as nitroglycerin, nitrates, nitrites, papaverine, isoproterenol, nylidrin, isoxsuprine, L-arginine, nitroprusside, adenosine, dobutamine, xanthines, ethyl alcohol, dipyridamide, hydralazine, minoxidil and diazoxide and analogs thereof may be expected to benefit heart patients. In addition to these agents, endogenous vasodilators such as nitric oxide and prostaglandins can be induced by known pharmaceutical agents. Non-pharmaceutical vasodilation, such as by the simple application of heat or hyperthermia-inducing medications will provide a substantial benefit in enhancing the perfusion of D-Ribose into tissue. For example, the patient having peripheral vascular disease may obtain the benefits of this method by applying a heating pad or warm compress to the area of stenosis, while self-administering D-Ribose.

EXAMPLE 7
Preoperative Conditioning with Ribose

Thirty study patients are selected from those scheduled for the therapies listed in Table I, excluding those patients in the excluded group of Example 1. The patients are divided into three groups: twenty are preloaded with D-Ribose and ten with D-Glucose as a control. Ribose may be administered in any convenient manner for any effective time. The dobutamine studies of Example 3 showed that three hours of pre-loading showed beneficial effect, while the normal healthy males of Example 2 were preloaded for three days. However, it is thought that for raising the hypoxic threshold, any length of time, even five minutes preoperative, will reduce or eliminate those effects of hypoxia, such as free-radical formation, that are not due to depressed energy levels. These free-radicals and other metabolites that accumulate during hypoxia are thought to be a possible cause of reperfusion injury, which delays recovery of the patient.

It is desirable to combine the benefits of longer term preloading to enhance energy, as is disclosed in the '789 Application, with the benefits of the presence of ribose during the hypoxic event. Therefore, when surgery is scheduled on a non-emergency basis, at least two weeks before scheduled surgery, the patient will take one to 60, preferably 10 to 30 grams, of D-Ribose or D-Glucose orally, preferably within 30 minutes prior to the administration of a vasodilator. NitroDur® nitroglycerin patches (Key Pharmaceuticals, Miami) are an especially convenient means of administration of a vasodilator, but any vasodilator may be administered. Once the patients are admitted to the hospital for surgery, it may be most convenient to administer the solutions intravenously. Ten of the ribose group are given 5% D-Ribose in 5% D-Glucose. Ten of the ribose group are given 5% D-Ribose in 5% Glucose plus a vasodilating agent. The preferred vasodilator is dobutamine at one to 10 $\mu$g/kg/minute. The control group of patients is given 10% D-Glucose. The administration of the test solutions is continued before, during and after the surgical procedure.

It is believed that the group given ribose will show better surgical outcome, faster recovery time, maintenance or improvement of myocardial function compared to the pre-operative state and a decreased need for pharmaceutical or additional support following surgery than the control group given glucose.

EXAMPLE 8
Stress Induced Ischemia

From the results of the clinical tests of Example 3, it is apparent that D-Ribose protected the heart from the stress-induced ischemia seen with dobutamine at higher doses. In patients given dobutamine alone, the frequency of inducible ischemia was seen to be 71% of the segments analyzed. D-Ribose decreased the number of segments showing inducible ischemia to 46%. It is to be expected, therefore, that administration of D-Ribose will have a beneficial effect whenever high doses of therapeutic agents are used that lead to stress-induced hypoxia.

EXAMPLE 9
Peripheral Vascular Disease

In peripheral vascular disease, poor circulation may be limited to the area of stenosis or vascular lesion. Therefore, such patients can obtain the benefits of ribose in raising the hypoxic level of the skeletal muscle with or without co-administration of a vasodilator. Following ingestion of three to ten grams of ribose, warm compresses or a heating pad are applied for at least 30 minutes to the area of the leg or legs having poor circulation. This method may be applied before exercise, but maximal benefit will occur if the method is applied daily.

All of the compositions and methods disclosed and claimed herein can be made and executed without undue experimentation in light of the present disclosure. While the compositions and methods of this invention have been described in terms of preferred embodiments, it will be apparent to those skilled in the art that variations may be applied to the compositions and methods described herein without departing from the concept and scope of the invention. More specifically, it will be apparent that certain agents that are both chemically and physiologically related may be substituted for the agents described herein while the same of similar results would be achieved. All such similar substitutes and modifications apparent to those skilled in the art are deemed to be within the scope and concept of the invention as defined by the appended claims.

We claim:

1. A therapeutic method comprising administering ribose to a mammal in an effective amount to increase the tolerance of the mammal to hypoxia so that ribose is present in the tissue of the mammal during the hypoxic event.

2. The method according to claim 1 wherein the mammal is a human.

3. The method according to claim 2 wherein ribose is administered in a dosage of about one to 60 grams.

4. The method according to claim 1 wherein ribose is administered at least five minutes prior to the occurrence of the hypoxic event.

5. A therapeutic method comprising administering ribose and a vasodilator to a mammal in an effective amount to increase the tolerance of the mammal to hypoxia so that ribose is present in the tissue of the mammal having reduced tissue circulation during the hypoxic event.

6. The method according to claim 5 wherein the mammal is a human.

7. A therapeutic method comprising administering ribose and an inotropic agents to a mammal in an effective amount to increase the tolerance of the mammal to hypoxia so that ribose is present in the tissue of the mammal having reduced tissue circulation during the hypoxic event.

8. The method according to claim 7 wherein the mammal is a human.

9. The method of claims 1, 5 or 7 wherein ribose is administered orally, intravenously or intraperitoneally.

10. The method of claims 1, 5 or 7 wherein the hypoxia is due to cardiovascular disease, myocardial stunning, anaesthesia, surgical procedures, peripheral vascular disease, intermittent claudication, pulmonary dysfunction, physical exertion, pharmaceutical treatment, tachycardia or poisoning.

* * * * *